United States Patent [19]

Takeuchi et al.

[11] Patent Number: 5,120,717
[45] Date of Patent: Jun. 9, 1992

[54] PHARMACEUTICAL COMPOSITION FOR INHIBITING INFECTION WITH VIRUS CAUSATIVE OF ACQUIRED HUMAN IMMUNODEFICIENCY SYNDROME

[75] Inventors: Tomio Takeuchi, Tokyo; Shinichi Kondo, Yokohama; Hiroo Hoshino, Maebashi, all of Japan

[73] Assignee: Zaidan Hojin Biseibutsu Kagaku Kenkyu Kai, Tokyo, Japan

[21] Appl. No.: 394,539

[22] Filed: Aug. 16, 1989

[30] Foreign Application Priority Data

Aug. 22, 1988 [JP] Japan .................. 63-206346

[51] Int. Cl.$^5$ .................. A61K 31/71; C07H 15/24
[52] U.S. Cl. .................. 514/27; 514/33; 514/34; 514/934; 536/6.4
[58] Field of Search .................. 514/33, 27, 34, 934; 536/6.4

[56] References Cited

U.S. PATENT DOCUMENTS 4,870,165  9/1989  Oki et al. .................. 514/27

FOREIGN PATENT DOCUMENTS 277621  8/1988  European Pat. Off. .............. 514/27
315147  5/1989  European Pat. Off. .............. 536/6.4

OTHER PUBLICATIONS

Hinuma, et al. Proc. Natl. Acad. Sci. USA 78(10) 6476-6480, 1981.
Tanabe, et al., J. of Antibiotics vol. 41, 1988 pp. 1706-1710.
Gomi, et al., J. of Antibiotics vol. 41, 1988 pp. 1019-1028.
Hoshino, et al. J. of Antibiotics, vol. 42, 1989 pp. 344 to 346.
Takeuchi, et al. J. of Antibiotics vol. 48, 1988 pp. 807-810.

Primary Examiner—Robert T. Bond
Assistant Examiner—E. C. Ward
Attorney, Agent, or Firm—Larson and Taylor

[57] ABSTRACT

Pharmaceutical compositions containing at least one of benanomicins A and B and their salts are now provided, which are useful to inhibit the infection of human T-cells with HIV, namely a virus causative of acquired human immunodeficiency syndrome (AIDS). Thus, benanomicins A and B as well as their salts are useful as antiviral agent against HIV.

2 Claims, No Drawings

PHARMACEUTICAL COMPOSITION FOR INHIBITING INFECTION WITH VIRUS CAUSATIVE OF ACQUIRED HUMAN IMMUNODEFICIENCY SYNDROME

SUMMARY OF THE INVENTION

This invention relates to a pharmaceutical composition for inhibiting infection with a virus causative of acquired human immunodeficiency syndrome, which composition comprises benanomicin A, benanomicin B or a salt thereof as active ingredient. This invention also includes an antiviral agent comprising benanomicin A, benanomicin B or a salt thereof as active ingredient which agent is useful to inhibit infection with a virus causative of the acquired human immunodeficiency syndrome. This invention further relates to a method for inhibitingly treating a virus causative of the acquired human immunodeficiency syndrome, with benanomicin A or benanomicin B or a salt thereof.

BACKGROUND OF THE INVENTION

Acquired human immunodeficiency syndrome (hereinafter sometimes called merely as "AIDS") has been found to be a disease which is caused due to human T-cells being infected by a causative virus in human blood. The virus which is causative of the acquired human immunodeficiency syndrome is usually termed as acquired human immunodeficiency syndrome virus which is often abbreviated as HIV. It has been reported that certain known compounds are useful as an agent for inactivating HIV or an antiviral agent against HIV. However, any of these compounds is not necessarily satisfactory as a useful remedial agent for AIDS.

AIDS is an important disease which brings about serious problems in human society, and there is a strong outstanding demand to develope and provide such a new drug which can show a high activity to inhibit infection with HIV and which are expectable as a useful medicinal agent for therapeutically or preventively treating patients with AIDS.

On the other hand, we, the present inventors, and our associates have discovered that when a strain of Actinomycetes, designated as MH193-16F4 strain, is cultured in a culture medium under aerobic conditions, two antibiotics named as benanomicin A and benanomicin B are produced and accumulated in the culture. Benanomicin A and benanomicin B as well as salts thereof have been found to have strong antifungal activities in vivo, and benanomicins A and B have been found to be represented by a general formula (I):

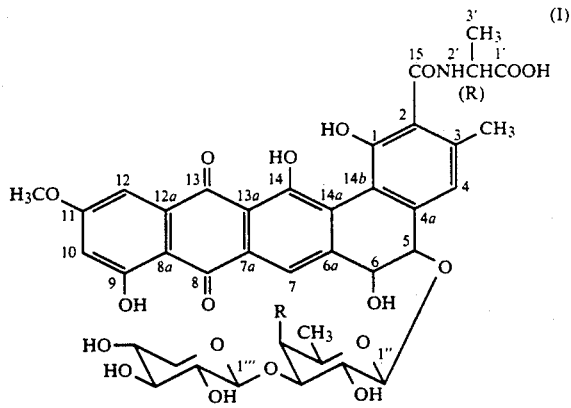

wherein R denotes a hydroxyl group for benanomicin A and R denotes an amino group for benanomicin B, Benanomicin A and benanomicin B as well as salts thereof are described in the "Journal of Antibiotics" Vol. 41, page 807 (June, 1988) and in the specification of our co-pending Japanese patent application No. 277,692/87 filed Nov. 2, 1987 (now laid-open under Japanese patent appln. first publication "Kokai" No. 121293/89 on 12 May 1989) and in the specification of the corresponding U.S. patent application Ser. No. 264,888 (filed Oct. 31, 1988) now U.S. Pat. No. 5,055,453 or the corresponding European patent application No. 88-118,253.9 filed Nov. 2, 1988 (now laid-open under European patent appln. publication No. 0 315 147 A2 on May 10, 1989).

Benanomicin A is an acidic substance in the form of a reddish brown powder which has a melting point higher than 220° C. and is only sparingly soluble in methanol, chloroform, ethyl acetate and acetone but is soluble in dimethylsulfoxide, dimethylformamide and alkaline water and insoluble in water. Benanomicin B is an amphoteric substance and benanomicin B hydrochloride is in the form of a reddish brown powder which has a melting point higher than 220° C. and a specific rotation $[\alpha]^{22}_D + 360°$ (c 0.05, water) and is only sparingly soluble in chloroform, ethyl acetate and acetone and is soluble in methanol, dimethylsulfoxide, dimethylformamide and water.

DETAILED DESCRIPTION OF THE INVENTION

We have now discovered that benanomicin A, benanomicin B and a salt thereof exhibit a high inhibitory activity to infection of human T-cells with HIV, and that more particularly, when human T-cells which have been treated with benanomicin A, benanomicin B or a salt thereof in a culture medium are brought into contact with HIV, infection of the human T-cells with HIV can be inhibited under the action of benanomicin A or benanomicin B or a salt thereof.

We have also found that syncytium formation of human T-cells by co-cultivation of human T-cells with HIV-infected T-cells has been strongly inhibited through the treatment with benanomicins A and B and salts thereof. These results suggest that benanomicins A and B inhibit adsorption of HIV to the T-cells at earlier stages of HIV-infection. Benanomicins A and B have antifungal activities against Candida, Cryptococcus or Aspergillus. These fungi have been frequently detected in patients with AIDS. Thus, if further analyses show that benanomicins can be used as an antiviral agent for AIDS, their administration may be especially advantageous for patients with AIDS or AIDS-related complex who are infected with fungi or are at risk for fungal infection. In this sense, benanomicins A and B and salts thereof have an activity to inhibit the infection of human T-cells with HIV and, in a broad sense, have an antiviral activity against HIV.

According to a first aspect of this invention, therefore, there is provided a pharmaceutical composition for inhibiting the infection with a virus causative of acquird human immunodeficiency syndrome, which comprises as active ingredient at least one of benanomicin A and benanomicin B having the general formula (I)

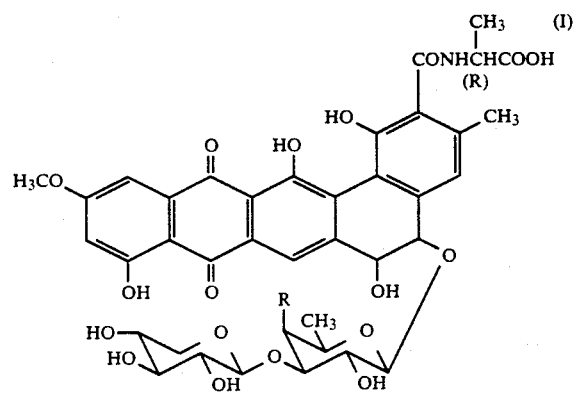

wherein R is a hydroxyl group for benanomicin A or an amino group for benanomicin B, and salts thereof, in association with a pharmaceutically acceptable carrier for the active ingredient.

In another aspect of this invention, there is provided an antiviral composition for inhibiting syncytium formation of human T-cells induced by a virus causative of acquired human immunodeficiency syndrome, which comprises an effective amount of at least one of benanomicin A, benanomicin B and pharmaceutically acceptable salts thereof as active ingredient, in association with a pharmaceutically acceptable carrier for the active ingredient.

In a further aspect, this invention include a method for inhibiting infection of human T-cells with a virus causative of aquired human immunodeficiency syndrome, which comprises treating human T-cells with benanomicin A, benanomicin B or a pharmaceutically acceptable salt thereof in an amount effective to inhibit the infection with said virus.

In another further aspect, this invention includes a method for inhibiting syncytium formation of human T-cells induced by a virus causative of acquired human immunodeficiency syndrome, which comprises treating the human T-cells with benanomicin A, benanomicin B or a pharmaceutically acceptable salt thereof in an .amount effective to inhibit the syncytium formation of human T-cells induced by said virus.

This invention further includes use of benanomicin A, benanomicin B or a pharmaceutically acceptable salt thereof as an antiviral agent against a virus causative of acquired human immunodeficiency syndrome.

Benanomicn A which is useful as the active ingredient according to this invention is an acidic compound containing a carboxyl group, so that benanomicin A can form various salts at its carboxyl group by reaction with a basic compound. While, benanomicin B which is useful as another active ingredient according to this invention is an amphoteric compound containing a carboxyl group and an amino group, so that benanomicin B can form various salts at its carboxyl group by reaction with a basic compound and also can form an acid addition salt at its amino group by reaction with an acidic compound. The salts that benanomicin A of the acidic nature can form at its carboxyl group include a pharmaceutically acceptable salt (the carboxylate) such as an alkali metal salt, e.g. sodium salt and an alkaline earth metal salt, e.g., calcium salt, as well as a base addition salt (at the carboxyl group) with a pharmaceutically acceptable organic amine such as lower alkylamines. The salts that benanomicin B of the amphoteric nature can from at its carboxyl group and/or at its amino group include a pharmaceutically acceptable salt (the carboxylate) such as an alkali metal salt and an alkaline earth metal salt, as well as a base addition salt (at the carboxyl group) with a pharmaceutically acceptable organic amine and also include an acid addition salt (at the amino group) with a pharmaceutically acceptable inorganic acid such as hydrochloric acid and sulfuric acid or with a pharmaceutically acceptable organic acid such as acetic acid, malic acid and the like.

Benanomicin A and benanomicin B are both characterized by their low toxicity to mammalian animals. For instance, in the tests of estimating acute toxicity of benanomicins where mice were intravenously administered with benanomicin A or benanomicin B, it have been found that the mice having received administration of a benanomicin tolerated a dosage of 600 mg/kg of benanomicin A or a dosage of 100 mg/kg of benanomicin B without involving their death.

The pharmaceutical compositions according to this invention which contain either benanomicin A or benanomicin B or a salt thereof as the active ingredient in combination with a pharmaceutically acceptable solid or liquid carrier for the active ingredient may be formulated in a conventional manner into conventional forms of medicinal preparation such as powders, granules, tablets, syrups, injections and the like for oral administration or parenteral administration.

The following assay tests were conducted in order to demonstrate that benanomicin A and benanomicin B have an inhibitory activity to infection of human T-cells with HIV, namely the acquired human immunodeficiency syndrome virus. The procedure for these assay tests is as follows:

Tests

Effects of benanomicin A and benanomicin B inhibitory to infection of human T-cells with HIV were examined in a similar manner to the assay methods described in the "Proc. Natl. Acad, Sci. U.S.A.," 80, 6061–6065 (1983); "J. Antibiot.", 40, 1077–1078, (1987); and "J. Antibiot.", 42, 344–346, (1989).

About $1 \times 10^5$ cells/ml of MT-4 cells (human T-cell line) in phosphate buffered saline were seeded into Costar 48-well plates in an amount of 0.5 ml/well. Each well was added with 50 μl of benanomicin A or benanomicin B solution (dissolved at concentration of 10 mg/ml in dimethysulfoxide and diluted with phosphate buffered saline). Two hours later, MT-4 cells were infected with 50 μl of HIV (1,000–10,000 plaque-forming units) in each well. The plates were incubated for 4 days at 37° C. under 5% $CO_2$. The MT-4 cells were smeared onto slide glasses, dried and fixed with acetone. The presence of HIV antigen-positive cells were detected by the indirect immunofluoroescent assay [Y. Hinuma et al., "Proc. Natl. Acad. Sci. U.S.A.," 78, 6476-6480, (1981)]. Cell smears were treated at 37° C. for 30 minutes with serum of AIDS patient at a dilution of 1:10 in phosphate buffered saline as the first antibody. After washing with phosphate buffered saline, the cells were treated at 37° C. for 30 minutes with fluorescent isothiocyanate-conjugated rabbit anti-human immunoglobulin serum (Cappel Laboratories, Cochranville, Pa., U.S.A.) as the second antibody. After the cell smears were washed with phosphate buffered saline and covered with a cover glass, the cells were examined under a fluorescence microscope. Percentages of the number of viral antigen-positive cells (namely, immunofluorescent cells where the HIV-associated antigens were expressed) in total cells were calculated.

Furthermore, cytotoxicity of benanomicin A or benanomicin B to the MT-4 cells was estimated by incubating the MT-4 cells at varying concentrations of benanomicin A or benanomicin B added and in the absence of HIV but in the same manner of incubation and under the same conditions of incubation of MT-4 cells as those employed in the above-mentioned test procedure of assaying the activity of benanomicin A or B to inhibit infection of T-cells with HIV.

The results of the above tests of assaying the inhibitory activities of benanomicin A and benanomicin B to the HIV-infection as well as the tests of estimating the cytotoxicities of these benanomicins are shown in a table below.

TABLE

| Concentration of benanomicin (μg/ml) | Benanomicin A | | Benanomicin B | |
|---|---|---|---|---|
| | Viral antigen-positive cells (%) | cytotoxicity | Viral antigen-positive cells (%) | Cytotoxicity |
| 100 | 1 | ± | <1 | + |
| 10 | 30 | — | 1 | — |
| 1 | 80 | — | 65 | — |
| 0.1 | >90 | — | >90 | — |
| 0 | >90 | — | >90 | — |

As is apparent from the test results of the above table, it has been confirmed that benanomicin A and benanomicin B are both free of the cytotoxicity at their concentration of 10 μg/ml and can significantly reduce the number of viral antigen-positive cells. Accordingly, it has been confirmed that benanomicin A and benanomicin B both have high activities to inhibit infection of human T-cells with HIV.

Inhibitory effects of benanomicin A and benanomicin B on syncytium formation of human T-cells induced by HIV were examined in the same manner as described in the "J. Antibiot.", 42, 344-346, (1989) according to the following procedure:

The Molt-4 human T-cells were seeded into Costar 8-well plates in an amount of 100,000 cells/well. Benanomicin A or B solution was added. After 2 hours, Molt-4 cells which have persistently been infected with HIV were added at 15,000 cells/well. The number of syncytia or multinucleated giant cells which were formed in 5×5 mm space in each well after cultivation for 24 hours was counted under a microscope. Cells whose diameters were approximately 5 times or more as large as those of the Molt-4 cells which were not co-cultivated with HIV-producing Molt-4 cells were considered to be syncytia.

Benanomicins A and B inhibited syncytium formation of the T-cells at concentrations of 10-100 μg/ml.

In general, benanomicin A or benanomicin B can be administered either orally or parenterally upon its actual administration in the form of an antiviral composition for inhibiting the infection with HIV.

When the active ingredient compound used according to this invention, namely benanomicin A or B or a salt thereof is given as the antiviral agent against HIV, it can be administered alone or it can be administered in the form of an injection, oral preparation, suppository or the like containing an excipient or carrier as mixed together. Any pharmaceutically acceptable excipient and carrier are available for that purpose. The nature and composition of the carrier used may vary depending on the administration route and manner. For example, water, ethanol, an animal or vegetable oil such as soybean oil, sesame oil or mineral oil, or a synthetic oil may be used as a liquid carrier. Suitable solid carriers include, for example, a sugar such as maltose or sucrose, an amino acid, a cellulose derivative such as hydroxypropylcellulose, a polysaccharide such as cyclodextrin, a salt of an organic acid such as magnesium stearate, or the like. In the case of the injections, it is generally preferable that the liquid medium of the injections comprises physiological saline, a buffered solution, an aqueous solution of a sugar such as glucose, inositol or mannitol, or a glycol such as ethylene glycol or polyethylene glycol. It is also feasible to formulate a lyophilized preparation containing a benanomicin as the active ingredient mixed along with an excipient, e.g., a sugar such as inositol, mannitol, glucose, mannose, maltose or sucrose or an amino acid such as phenylalanine. Upon administration, such lyophilized preparation may be dissolved in a suitable solvent for injection, for example, sterilized water or an intravenously-administerable liquid such as physiological saline, aqueous solution of glucose, an aqueous solution of electrolytes or an aqueous solution of amino acids.

Although the proportion of benanomicin A or benanomicin B present in the formulated composition may widely vary from one preparation to another preparation, it may generally be in a range of 0.1-100 wt. %, preferably 1-90 wt. %. In the case of an injection, for example, it is generally desirable that the injectionable solution contains the compound as active ingredient at a concentration of 0.1-5 wt. %. For oral administration, the compound as active ingredient may be formulated into tablets, capsules, a powder, granules in combination with the solid carrier or may be formulated into a solution, a dry syrup or the like in combination with the liquid carrier. In capsules, tablets, granules or a powder, the proportion of benanomicin as the active ingredient present therein may generally be in a range of about 3-100 wt. %, preferably 5-90 wt. %, with the balance being formed of a carrier.

The dosage of benanomicin A or benanomicin B may suitably be determined in account of the age, body weight, symptom of patients and therapeutic purpose as intended. The therapeutic, i.e., effective dosage of a benanomicin may be generally in a range of 1-300 mg/Kg/day for the i parenteral administration and in a range of 5-500 mg/Kg/day for the oral administration. This dosage can be administered either continuously or intermittently as long as the total dosage does not exceed such a specific level that was decided in view of results of animal tests and various circumstances. Similarly, the total dosage given in the parenteral administration may, of course, vary suitably depending on the way of administration, conditions of the patient or animal under treatment, for example, the age, body weight, sex, sensitivity, fpods or feed, administration time, administration route, drugs administered concurrently, conditions of the patient and disease. The suitable dosage and administration frequency of a benanomicin under given conditions must be determined by an expert physician through the tests of determining optimal dosage and in light of the above guidelines. These requirements for administration should also applies to the oral administration of a benanomicin.

This invention is now illustrated with reference to the following Examples which show various forms of the preparations or compositions according to this invention.

EXAMPLE 1

An amount of purified water was added to 50 parts by weight of sodium salt (the carboxylate) of benanomicin A to give a total of 2,000 parts by weight. After dissolution of the sodium salt in water, the solution thus prepared was subjected to sterilizing filtration by passing through a microporous filter of a tradename "Millipore Filter GS". Two grams of the sterile filtrate obtained were taken into each 10 ml vial and then lyophilized, to obtain a lyophilized preparation for injection which contained 50 mg of sodium salt of benanomicin A per vial.

EXAMPLE 2

Fifty parts by weight of benanomicin A, 600 parts by weight of lactose, 330 parts by weight of crystalline cellulose and 20 parts by weight of hydroxypropylcellulose were mixed together thoroughly. The resultant powdery mixture was pressed by a roll-type pressing machine (Roller Compactor, trade mark) and then the resulting compressed solids were crushed. The thus-crushed material was sifted. The fraction of the resulting granules which were of sizes between 16 mesh and 60 mesh was collected as granular preparation.

EXAMPLE 3

Thirty parts by weight of benanomicin A, 120 parts by weight of crystalline lactose, 147 parts by weight of crystalline cellulose and 3 parts by weight of magnesium stearate were mixed together in a V-model mixer and compressed into tablets each containing 300 mg of benanomicin A as the active ingredient per tablet.

EXAMPLE 4

An amount of purified water was added to 30 parts by weight of benanomicin B hydrochloride to give a total of 2,000 parts by weight. After dissolution of the benanomicin B hydrochloride in water, the solution thus prepared was subjected to sterilizing filtration by passing through a microporous filter of a tradename "Millipore Filter GS".

Two grams of the sterile filtrate were taken into each 10-ml vial and then lyophilized, to give a lyophilized preparation for injection which contained 30 mg of benanomicin B hydrochloride per vial.

EXAMPLE 5

Fifty parts by weight of benanomicin B hydrochloride, 600 parts by weight of lactose, 330 parts by weight of crystalline cellulose and 20 parts by weight of hydroxypropylcellulose were mixed together thoroughly. The resultant powdery mixture was pressed by a roll-type pressing machine (Roller Compactor, trade mark) and then the resulting compressed solids were crushed. The thus-crushed material was sifted. The fraction of the granules which were of sizes between 16 mesh and 60 mesh was collected as granular preparation.

EXAMPLE 6

Thirty parts by weight of benanomicin B hydrochloride, 120 parts by weight of crystalline lactose, 147 parts by weight of crystalline cellulose and 3 parts by weight of magnesium stearate were mixed in a V-model mixer and compressed into tablets each containing 300 mg of benanomicin B hydrochloride the active ingredient per tablet.

Since benanomicins A and B are antibiotics which are produced by cultivation of a new microorganism, MH193-16F4 strain, the fermentative production of these antibiotics are described hereinafter.

The production of benanomicins A and B may be carried out by inoculating the MH193-16F4 strain of Actinomycetes to a culture medium containing such nutrient sources which can be utilized by ordinary microorganisms, and then incubating said benanomicin-producing strain under aerobic conditions. Benanomicin A and B are produced and accumulated primarily in the culture broth. Benanomicins A and B may be recovered from the resulting culture, especially from the culture broth or its filtrate.

The nutrient sources available in the culture medium to be used may be any of the conventional carbon and nitrogen sources which have been useful as nutrient sources for the cultivation of known strains of Actinomycetes. For example, the assimilable nitrogen sources may include soybean meal, peptone, meat extract, corn steep liquor, cotton seed meal, peanut meal, dry yeast, yeast extract, NZ-amine, casein, sodium nitrate, ammonium sulfate and ammonium nitrate which are commercially available. The assimilable carbon sources may include glycerin, sucrose, starch, glucose, galactose, maltose, dextrin, lactose, molasses, soybean oil, fats and amino acids, which are commercially available. The culture medium may also contain inorganic salts such as sodium chloride, phosphates, calcium carbonate, magnesium sulfate, cobalt chloride and manganese chloride. In addition, trace amounts of metal salts, and one or more of animal, vegetable or mineral oils as antifoaming agents can also be added.

Liquid cultivation method is preferred for the production of benanomicins A and B in a large scale. The cultivation temperature may be chosen within the range of the temperatures at which the benanomycins-producing microorganism can grow and can produce benanomicins A and B. The cultivation temperature may generally be at 20°-40° C., preferably at 25°-37° C.

For recovery of benanomicins A and B from the resulting culture of the microorganism capable of producing benanomicins A and B, benanomycins A and B can be extracted from the culture or the culture broth filtrate and then purified by using conventional methods for recovery and purification, for example, solvent extraction, ion-exchange resin method, adsorptive or partition columh chromatography, gel filtration, dialysis, precipitation and the like, either singly or in combination. For example, benanomicins A and B can be recovered from the incubated mycelial cake by extacting with acetone-water or methanol-water. On the other hand, benanomicins A and B which have been produced and accumulated in the culture broth or the filtrate can be adsorbed on an adsorbent such as a microporous non-ionic resinous adsorbent, for example, "DIAION HP-20" (trade name; synthetic resinous adsorbent produced by Mitsubishi Kasei Corporation, Japan). In addition, when the culture broth or the broth filtrate is extracted with an organic solvent immiscible with water, e.g., butanol, ethyl acetate or the like, benanomicin A and B substances are extracted in the organic solvent phase.

For the production of benanomicins A and B, it is preferred that the MH193-16F4 strain is cultivated in a culture medium under aerobic conditions at a temperature of 25° to 37° C., preferably for 3 to 10 days, to produce and accumulate benanomicin A and benanomicin B in the resulting culture broth, the culture broth is filtered, and the resultant culture broth filtrate is passed through a column of an adsorbent to effect the adsorption of benanomicin A and benanomicin B by the adsorbent, and benanomicin A and benanomicin B are separately recovered by chromatographically eluting the column of the adsorbent containing benanomicins A and B adsorbed therein.

For mutual isolation and further purification of benanomicins A and B, chromatographic method with use of an adsorbent such as silica gel ("WAKOGEL C-300", trade name, product of Wako Pure Chemical Industries, Ltd.), and alumina or a gel-filtration agent "Sephadex LH-20" (trade name; product of Pharmacia AB), or the like may be made suitably.

Benanomicins A and B as produced in the culture as described above can be isolated as benanomicins A and B as such in their free form.

Incidentally, the MH193-16F4 strain has been deposited in an authorized Japanese depository "Fermentation Research Institute", Agency of Industrial Science and Technology, Ministry of International Trade and Industry, Japanese Government, under the deposit number FERM P-9529 since Aug. 21, 1987. The MH193-16F4 strain has now been deposited in the "Fermentation Research Institute" in terms of the Budapest Treaty under the deposit number "FERM BP-2051". This Japanese depository locates in Tsukuba-city, Ibaragi-ken, Japan.

When a solution containing benanomicins A and/or B or its concentrated solution is treated with a basic compound, for example, an inorganic base, including an alkali metal compound such as sodium hydroxide or potassium hydroxide, an alkaline earth metal compound such as calcium hydroxide or magnesium hydroxide, and an ammonium salt; as well as an organic base such as ethanolamine, triethylamine or dicyclohexylamine during the operation of one of steps for the recovery, for example, during the step of the extraction, isolation or purification, it happens that benanomicin A and/or B are or is converted into the corresponding salts which may then be separated or isolated in the form of such salts or salt.

The following Examples 7-9 illustrate the fermentative production of benanomicins A and B.

EXAMPLE 7

A loopful quantity of the MH193-16F4 strain (identified as FERM BP-2051), which had been incubated in a slant agar medium, was inoculated into 80 ml of a liquid culture medium comprising 1.0% starch and 3.0% soybean meal (pH 7.0 before the sterilization) which was placed in a Sakaguchi's flask of 500 ml-capacity. The inoculated culture medium was incubated at 28° C. for 3 days under rotatory shaking (135 rpm.) to provide a first seed culture. The first seed culture obtained was inoculated in 3 ml-portions into 80 ml-portions of the liquid culture medium having the same composition as above, which were separately placed in many Sakaguchi's flasks. The inoculated culture media were incubated for 3 days under the same incubation conditions as above, to give the second seed culture. The resultant second seed culture (2 liters) was then inoculated to a culture medium (50 liters) of the same composition as above which had been sterilized at 120° C. for 15 minutes and was placed in a tank-fermentor of 100 l-capacity. The so inoculated culture medium was then cultured at 28° C. for 2 days under aeration at a rate of 50 l of air per minute and under agitation at 200 rpm. to effect the submerged cultivation of the MH193-16F4 strain under aerobic conditions and obtain a third seed culture. The resultant third seed culture (12 liters) was inoculated into a productive culture medium (300 liters) comprising 2.0% of glycerin, 1.5% of soybean meal (available commercially under a tradename "Esusan Meat", a product of Ajinomoto Co. Ltd., Japan), 0.0025% of $K_2HPO_4$, 0.1125% of $KH_2PO_4$, 0.005% of $CoCl_2.6H_2O$, 0.03% of a silicone oil "KM72" (an anti-foaming agent, a trade name of a product of Shinetsu Chemicals Co. Ltd., Japan) and 0.01% of a surfactant "Adekanol" (a trade name, product of Asahi Denka Kogyo Co. Ltd., Japan) which had preliminarily been sterilized at 125° C. for 30 minutes and was placed in a tank-fermentor of 570 l-capacity. The cultivation was conducted at 28° C. for 7 days under agitation at 300 rpm. and under aeration at a rate of 150 l of air per minute for the first 24 hours of the cultivation and then at a rate of 300 l of air per minute after the 24th hour of the cultivation. After the completed cultivation, the culture broth obtained was mixed with diatomaceous earth as a filtration-aid and then filtered to give 250 l of the culture broth filtrate (pH 6.0).

EXAMPLE 8

The culture broth filtrate (250 l) obtained in the above Example 7 was passed through a column of 15 l of a microporous non-ionic adsorbent resin "DIAION HP-20" to effect the adsorption of the active substances by the adsorbent. After the adsorbent column was washed with 100 l of water and with 45 l of 50% aqueous methanol, the adsorbent column was eluted with 45 l of 70% aqueous methanol and then with 90 l of dry methanol, so that the first fraction (53 l), second fraction (38 l) and third fraction (27 l) of the eluate were obtained separately. The first fraction containing the active substance was concentrated to 3 l under reduced pressure, followed by adjustment to pH 3.5 with dilute hydrochloric acid to deposit a precipitate of a red color. The precipitate was collected by filtration and then dried under reduced pressure, whereby 152 g of a crude brown powder mainly comprising benanomicin A was obtained.

150 Grams of the crude powder was dissolved in 600 ml of dimethylformamide. After saturation of the resultant solution with water vapor at room temperature for 3 days in a desiccator, a crystalline precipitate was deposited. The precipitate was collected by filtration and then dried under reduced pressure, thereby obtaining 29 g of benanomicin A-dimethylformamide solvate. The second fraction of the eluate was processed in the same way as the first fraction, thereby obtaining 14 g of benanomicin A-dimethylformamide solvate.

One gram of the benanomicin A-dimethylformamide solvate as obtained from said first fraction was dissolved in dimethylsulfoxide (5 ml). The resultant solution was added dropwise under stirring into 300 ml of methanol, followed by stirring for 10 minutes to deposit a precipitate of a reddish brown color. The precipitate was filtered out and then dried under reduced pressure, to afford 935 mg of a purified benanomicin A as reddish brown powder.

A solution of benanomicin A (82.7 mg) in a mixture of 10 ml of water and 1.1 ml of 0.1M NaOH was lyophilized. The residue was dissolved in 3 ml of methanol and chromatographed on a Sephadex LH-20 column (300 ml) developed with methanol to obtain benanomicin A sodium salt (75.8 mg).

EXAMPLE 9

The third fraction of the eluate as obtained in the Example 8 was concentrated to 1.5 l under reduced pressure, followed by its adjustment to pH 3.5 with dilute hydrochloric acid, to obtain a precipitate of red color. The precipitate was collected by filtration and then dried under reduced pressure, whereby 98 g of a crude brown powder containing benanomicin B was obtained. One gram of this crude powder was dissolved in 10 ml of dimethylformamide at 40° C. and the resulting solution was passed through a column of 1 l. of a gel-filtration agent "Sephadex LH-20" which had been soaked with dimethylformamide, and then the "Sephadex" column was developed with dimethylformamid. The eluate was collected in 6 ml-fractions. Fraction Nos. 64–72 containing the active substance were collected, combined and then concentrated to dryness under reduced pressure, whereby 657 mg of a crude brown powder comprising benanomicin B-dimethylformamide solvate was obtained. Three hundred milligrams of this crude powder were dissolved in 100 ml of methanol, and after addition of 1 ml of 1N hydrochloric acid, the solution was concentrated to dryness under reduced pressure. The resultant crude powder of a brown color was dissolved in 3 ml of dimethylsulfoxide. The resulting solution was added dropwise to 200 ml of chloroform under stirring, followed by stirring for 20 minutes to deposit a reddish brown precipitate. The precipitate was collected by filtration and then dried under reduced pressure, to yield 258 mg of benanomicin B hydrochloride in a purified form.

We claim:

1. A method for inhibiting infection of human T-cells with virus causative of acquired human immunodeficiency syndrome, which comprises treating human T-cells with benanomicin A, benanomicin B or a pharmaceutically acceptable salt thereof in an effective amount to inhibit the infection with said virus.

2. A method for inhibiting syncytium formation of human T-cells induced by a virus causative of aquired human immunodeficiency syndrome, which comprises treating the human T-cells with benanomicin A, benanomicin B or a pharmaceutically acceptable salt thereof in an amount effective to inhibit the syncytium formation of human T-cells inducd by said virus.

* * * * *